United States Patent [19]

Chapman et al.

[11] Patent Number: 5,414,142
[45] Date of Patent: May 9, 1995

[54] PROCESS FOR THE PREPARATION OF MEDIUM SIZED CARBOCYCLIC ALKYL ETHERS

[75] Inventors: John J. Chapman, Greensboro; Jack R. Reid, Whitsett, both of N.C.

[73] Assignee: Lorillard Tobacco Company, New York, N.Y.

[21] Appl. No.: 84,662

[22] Filed: Jun. 28, 1993

Related U.S. Application Data

[63] Continuation of Ser. No. 859,646, Mar. 23, 1992, abandoned, which is a continuation of Ser. No. 551,404, Jul. 12, 1990, abandoned.

[51] Int. Cl.$^6$ .............................................. C07C 41/14
[52] U.S. Cl. ...................................... 568/579; 568/659
[58] Field of Search ............................... 568/659, 579

[56] References Cited

U.S. PATENT DOCUMENTS 3,876,561 4/1975 Naegeli ............................. 568/579
3,993,604 11/1976 Thomas et al. ................... 568/579

OTHER PUBLICATIONS

Streitwieser et al., *Introduction to Organic Chemistry* pp. 147–148 (1976).

*Primary Examiner*—Johann Richter
*Assistant Examiner*—John Peabody
*Attorney, Agent, or Firm*—White & Case

[57] ABSTRACT

An economically advantageous method is disclosed for the preparation without added solvent of a carbocyclic ether having from 10 to 16 carbon atoms in the ring of the formula

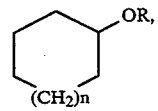

wherein R is a straight or branched ($C_3$–$C_6$) chain alkyl group or a benzyl group and n is from 5–11 carbon atoms, which method comprises: (1) reacting under an inert atmosphere a mixture consisting essentially of a carbocyclic alcohol of the formula

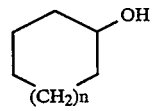

wherein n is from 5–11 carbon atoms, about 1.5–10 molar equivalents of a straight or branch ($C_3$–$C_6$) chain alkyl halide or benzyl halide and a metal hydride.

14 Claims, No Drawings

PROCESS FOR THE PREPARATION OF MEDIUM SIZED CARBOCYCLIC ALKYL ETHERS

This application is a continuation of application Ser. No. 07/859,646, filed on Mar. 23, 1992, now abandoned, which is a continuation of application Ser. No. 07/551,404, filed Jul. 12, 1990, now abandoned.

BACKGROUND OF THE INVENTION

Medium sized ($C_{10}$–$C_{16}$) ring carbocyclic alkyl ethers have found utility in perfume and fragrance formulations (Stroll, M.; Rouve, A. Synthesis of Macrocyclic Products of a Musk Odor. Cyclic Acyloins. Helv. Chim. Acta. 1947, 30, 1822; Haarmann; Reimer Neth. Patent 6,411,715, 1965. Chem. Abstr. 63:8228d (1965)). Their potential in textiles, coatings, and paper applications as odor enhancing materials and non-ionic surfactants are also encouraging (Tong, S. T. Macrocyclic Compounds from Pine Needle Wax. Soap Perfum. Consmet. 1954, 27, 58 Chem. Abstr. 49:2339a (1954)). In the past, these ethers have been prepared by reacting sulfate esters with alkoxide ions, (Williamson, A. W.; J. Chem. Soc. 1852, 4 229), by the alkyloxymercuration of alkenes (March, J. Advanced Organic Chemistry Reactions, Mechanisms, and Structure, 2nd. Ed.; McGraw-Hill: New York, 1978, pp. 357-361), by the reaction of diazoalkanes with carbinols (Neeman, M.; Caserio, C. M.; Roberts, J. D.; Johnson, W. S. Tetrahedron Lett. 1959, 6,36. Chem. Abstr. 53: 17877a (1958)), by the reaction of copper (I) alkoxides with alkyl halides (Whitesides, G. M.; Sadowski, J. S.; Lilburn, J. J. Am. Chem. Soc. 1974, 96, 2829. Chem. Abstr. 81:13039 (1973)), by the reduction of esters with trichlorosilane (Baldwin, S. W.; Haunt, S. A. J. Org Chem. 1975, 40, 3885. Chem. Abstr. 84: 16797k (1975)), or enol ethers with metal catalysts (Verzele, M.; Acke, M.; Anteunis, M. J. Chem. Soc. 1963, 5598). A more general reaction includes an alkyl halide displacement of an alkoxide ion. All of these previous preparations require tedious column chromatographic techniques to obtain uncontaminated product and these preparative difficulties are evidenced by the small number of medium sized ($C_{10}$–$C_{16}$) ring syntheses found in the chemical literature.

It was our aim to develop an efficient and economical method to prepare medium sized ($C_{10}$–$C_{16}$) ring carbocyclic ($C_3$–$C_6$) alkyl ethers which utilized a minimum number of steps, contained no unwanted byproducts, and required a minimal work-up effort. Until now, all reported syntheses gave low yields of a product that was contaminated with starting alcohol, and was extremely difficult to separate and therefore not an attractive syntheses for commercial use.

DESCRIPTION OF THE INVENTION

A process for the synthesis of a medium-sized ($C_{10}$–$C_{16}$) ring carbocyclic alkyl ether which comprises: (1) refluxing a mixture of about 1.0 equivalent macrocyclic carbinol having ten to sixteen carbon atoms in about 1.5 to 10 equivalents of an alkyl halide together with about 1.5 to 4 equivalents of a neat, dry metal hydride, (2) refluxing the mixture vigorously for 1 to 6 hours in an inert atmosphere, (3) cooling the reaction mixture to below 5° C. and destroying excess metal hydride by the careful addition or an alcohol under an inert atmosphere, (4) removing the volatile organic material by evaporation and combining the residue with 3-5 times its volume of water, (5) extracting the resulting mixture with several portions of a suitable solvent, (6) washing the organic layer with several portions of a suitable saturated aqueous salt solution, (7) recovering the organic layer and drying it over an appropriate drying agent, and (8) filtering, evaporating the solvent at reduced pressure, and distilling to obtain the pure macrocyclic alkyl ether in near quantitative amounts.

The novel process is suitable for the preparation of medium sized ($C_{10}$–$C_{16}$) ring carbocyclic alkyl ethers from cyclic carbinols containing 10 to 16 carbon atoms by the following chemical reaction:

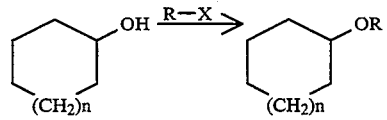

R can be an alkyl group having 3 to 6 carbons or a branched chain alkyl substituent such as propyl, butyl, isobutyl, or an aryl group such as benzyl or a substituted benzyl. The "n" can be 5–11 carbons and X can be iodine, bromine or chlorine.

The neat and dry sodium hydride is either purchased from a commercial source such as the Aldrich Chemical Company or is prepared by twice washing an oil suspension of the appropriate metal hydride with generous portions of hexane or other low boiling hydrocarbon and drying the hydride under an inert atmosphere. The alkyl halide is utilized as both the solvent and electrophile for the reaction and is used at 1.5–10 equivalents based on the molecular weight of the medium sized carbinol ring.

The excess metal hydride in the reaction can be destroyed using an alcohol such as ethanol or isopropanol and the extraction of the resulting product can be made using an organic solvent such as hexane, ether or ethyl acetate. The extracted organic solvent can be dried over a suitable standard drying agent for example magnesium sulfate, sodium sulfate, potassium carbonate, and sodium carbonate. Although 60% sodium hydride in mineral oil is preferred other hydrides such as potassium hydride may be used in 35% mineral oil. The invention will be more fully understood by reference to the following specific examples:

EXAMPLES

EXAMPLE 1

Phenylmethoxycyclododecane

60% sodium hydride (34.0 g dispersed in mineral oil, 0.85 mol) was washed twice with hexane under an argon atmosphere. The hexane was carefully decanted off and the hydride was dried by passing argon over its surface while stirring.

The hydride was mixed, under an argon atmosphere and by mechanical stirring, with cyclododecanol (130.0 g. 0.71 mol) and benzyl chloride (650.0 g, 5.14 mol). The reaction mixture was heated to 125° C. The mixture became very viscous when the temperature reached between 60° and 70° C. A mild exotherm was observed at about 100° C. which resulted in a marked viscosity decrease. If an efficient reflux condenser is not used, some external cooling may be necessary during the mild exotherm. The internal flask temperature increased to about 120° C. over ten minutes. The reaction flask was heated at 120° to 125° C. for an additional hour and then it was cooled to 25° C. The excess hydride was carefully destroyed by the addition of 100 mL of 95% ethanol under an argon atmosphere. The mixture was treated with 500 mL of aqueous saturated sodium chloride solution and extracted with three 400 mL portions of hexane. The organic layer was collected, washed with two 100 mL portions of water and two 100 mL portions of aqueous sodium chloride solution. The product mixture was dried over magnesium sulfate, filtered, and concentrated at 50° C. and 15 mm. The product was distilled at 144°-146° C./0.2 mm to give (180.7 g) 93.0% of the theoretical yield. Gas chromatography ("GC") showed that the product was 99% of a single component, IR (neat; cm$^{-1}$) 2930, 2865, 1475, 1455, 1095 (C-O-C), 1070, 740; 13C NMR (ppm CDC13) 139.21, 128.17, 127.54, 127.21, 76.26 (α-ring carbon), 70.22 (α-chain carbon), 28.91, 24.75, 24.31, 23.30, 23.19, 20.81; MS, m/z (relative intensity) 274 (M+, 1.5), 245(0.1), 230(0.4), 183(8.2), 174(0.9),160(1.0), 145(0.8), 133(2.3), 118(2.7), 104(10.4), 91(100), 81(3.2), 65(12.7), 56(2.1). Anal calcd for $C_{19}H_{30}O$:C,83.15;H,11.02. Found: C,83.33;H,11.18.

EXAMPLE 2 n-Propoxycyclododecane,

Cyclododecanol (2.6 g, 14.11 mmole), 1-bromopropane (2.11 g, 17.76 mmole), and 60% sodium hydride in mineral oil (1.13 g, 28.24 mmole) prepared as in Example 1 were reacted for 6 hours. A 2.9 g sample (91.0%) was isolated as in Example 1. GC showed 99% one component; bp 68°-70° C. at 0.05 mm.

EXAMPLE 3 n-Propoxycyclododecane

Cyclododecanol (2.6 g, 14.11 mmol), 1-iodopropane (1.74 g, 102.54 mmol), and 60% sodium hydride in mineral oil (750.0 mg, 18.75 mmol) prepared as in Example 1 were strongly refluxed for 3 hours. A 3.0 g sample (94.0%) was isolated as in Example 1. GC showed 99% one component; bp 69°-71° C. at 0.09 mm. IR (neat, cm$^{-1}$) 2955, 2882, 1485, 1460, 1350, 1105 (C-O-C); 13C NMR (ppm, CDC13) 77.02 (α-ring carbon), 70.32 (α-chain carbon), 29.18, 24.94, 24.49, 23.39, 20.98, 10.82. Anal calcd for $C_{15}H_{30}O$:C,79.58, H,13.36. Found: C,79.55; H,13.42.

EXAMPLE 4 n-Butoxycyclododecane

Cyclododecanol (184.3 g, 1.00 mol); 1-bromobutane (500.0 g, 3.65 mol) and 60% NaH in mineral oil (65.0 g, 1.63 mol) prepared as in Example 1 were refluxed for 4 hours. A 221.3 g sample (92.1%) was isolated as in Example 1. GC showed 99% one component; bp 83°-84° C. at 0.08 mm.

EXAMPLE 5 n-Butoxycyclododecane

Cyclododecanol (184.3 g, 1.00 mole); 1-iodobutane (500.0 g, 2.72 mol) and 60% NaH in mineral oil (50.0 g, 1.25 mol) prepared as in Example 1 were reacted for 2 hours. A 230.7 g sample (96.0%) was isolated as in Example 1. GC showed 99% one component; bp 84°-85° C. at 0.05 mm. IR (neat, cm$^{-1}$) 2960, 2880, 1470, 1450, 1340 (C-O-C), 1105, 720; 13C NMR (ppm, CDC13) 76.95 (α-ring carbon), 68.28 (α-chain carbon), 32.48, 29.08, 24.82, 24.36, 23.26, 20.87, 19.55, 13.97; MS, m/z (relative intensity) 240 (M+,3), 197(2), 166(9), 141(2), 138(4), 137(2), 127(3), 124 (5), 123 (5), 113 (16), 97 (11), 96(26), 95(18), 82(50) 81(25), 68(25), 67(32), 57(70), 55(47), 43 (26), 41(100), 39(20). Anal calcd for $C_{16}H_{32}O$:C,79.93; H, 13.42. Found: C,80.06; H,13.44.

EXAMPLE 6

3-Methylbutoxycylododecane

Cyclododecanol (200.0 g, 1.09 mol); 1-bromo-3-methylbutane (500.0 g, 3.31 mol) and 60% sodium hydride in mineral oil (72.0 g, 1.8 mol) prepared as in Example 1 were reacted for 2 hours. A 228.3 g sample (82.7%) was isolated as in Example 1. GC showed 98% one component; bp 128°-130° C. at 0.05 mm.

EXAMPLE 7

3-Methylbutoxycyclododecane

Cyclododecanol (25.0 g, 0.14 mol); 1-iodo-3-methylbutane (125.0 g, 0.63 mol), and 60% sodium hydride in mineral oil (21.5 g, 0.54 mol) prepared as in Example 1 were refluxed for 2 hours. A 34.2 g sample (96%) was isolated as in Example 1. GC showed 99% one component; bp 97°-98° C. at 0.08 mm. IR (neat, cm$^{-1}$) 2925, 2860, 1465, 1440, 1350, 1090 (C-O-C), 1010; 13C NMR (ppm, CDC13) 76.98 (α-ring carbon), 66.83 (α-chain carbon), 39.18, 29.05, 25.12, 22.70, 20.87, 24.77, 23.29, 24.34; MS, m/z (relative intensity) 254 (M+, 1.5), 239(0.01), 211(0.04), 197(0.06), 183(1.3), 138(1.5), 127(3.8), 124(2.1), 110(3.4), 96(10.3), 82 (20.5), 68(6.7), 43(100.0), 41(55.4). Anal calcd for $C_{17}H_{34}O$:C,80.24; H,13.47. Found: C,80.11; H,13.51.

EXAMPLE 8 n-Hexyloxycyclododecane

Cyclododecanol (20.0 g, 0.11 tool), 1-bromohexane (120.0 g, 0.727 mol), and 60% sodium hydride in mineral oil (5.6 g, 0.14 mol) prepared as in Example 1 were refluxed for 2 hours. A 28.4 g sample (96%) was isolated as in Example 1. GC showed 99% one component; bp 109°-111° C. at 0.03 min. IR (neat, cm$^{-1}$) 28 38, 2868, 1470, 1452, 1354, 1100 (C-O-C); 13C NMR (ppm, CDC13) 76.90 (α-ring carbon), 68.64 (α-chain carbon), 31.81, 30.31, 2 9.06, 26.00, 24.78, 24.31, 23.29, 22.71, 20.78, 14.10; MS, m/z (relative intensity) 268 (M+,1.1), 225(0.03), 211(0.2), 197(1.0), 183(0.4), 138(2.4), 124(3.6), 111(4.5), 110(6.4), 97(2.0), 96(19.9), 83(15.4), 82(46.5), 69(16.1), 68(17.1), 55(34.2), 54(6.2), 43(100.0), 41(40.3), 39(14.8). Anal calcd for $C_{18}H_{36}O$:C,80.53; H,13.52. Found: C, 80.77; H, 13.33.

EXAMPLE 9 n-Propoxycyclotridecane

Cyclotridecanol (900.0 mg, 4.54 mmol) 1-bromopropane (1.09g, 8.86 mmol), and 50% sodium hydride in mineral oil (320.0 mg, 6.67 mmol) prepared as in Example 1 were strongly refluxed for 3 hours. A 770.0 mg sample (71%) was isolated as in Example 1. GC showed 98% one component, bp 82°-84° C. at 0.05 mm. IR (neat, cm$^{-1}$) 2930, 2850, 1460, 1350, 1100 (C-O-C), 1025. Anal calcd for $C16H320$:C,79.93; H,13.42. Found: C,79.90; H,13.43.

EXAMPLE 10 n-Propoxycyclotetradecane

Cyclotetradecanol (89 g, 0.42 mol); 1-iodopropane (340.0 g, 2.0 mol) and 60% sodium hydride in mineral oil (55.0 g, 1.38 mol) prepared as in Example 1 were refluxed for 4 hours. A 105.8 g sample (99%) was isolated as in Example 1. GC showed 99% one component;

bp 99°–101° C. at 0.03 mm. IR (neat, cm$^{-1}$) 2930, 2860, 1460, 1380, 1360, 1350, 1105 (C-O-C), 1020. Anal calcd for $C_{17}H_{34}O$:C,80.24, H,13.47. Found: C,80.42,H,13.33.

EXAMPLE 11 n-Ethoxycyclopentadecane

Cyclopentadecanol (3.8 g, 16.79 mmol); iodoethane (10.0 g, 64.1 mmoles) and 60% sodium hydride in mineral oil (3.8 g, 94.98 mmol) prepared as in Example 1 were refluxed for 18 hours. A 4.1 g sample (95%) was collected as in Example 1. GC showed 99% one component, bp 105°–106° C. at 0.05 mm. IR (neat, cm$^{-1}$) 2930, 2850, 1460, 1350, 1100 (C-O-C), 1025. Anal calcd for $C_{17}H_{34}O$:C,80.24; H,13.47. Found: C,80.31; H,13.44.

EXAMPLE 12 n-Propoxycyclopentadecane

Cyclopentadecanol (25.0 g, 0.11 mol); 1-iodopropane (186.9 g. 1.10) and 60% sodium hydride in mineral oil (22.5 g, 0.56 mol) prepared as in Example 1 were reacted at reflux for 4 hours. A 28.3 g sample (96%) was isolated as in Example 1. GC showed 99% one component; bp 114°–115° C. at 0.09 mm. IR (neat, cm $^{-1}$) 2925, 2850, 1460, 1362, 1092 (C-O-C), 1030, 13C NMR (ppm, CDCl3) 78.62 (α-ring carbon), 70.30 (α-chain carbon), 32.17, 31.19, 29.75, 28.91, 28.54, 28.35, 27.45, 26.94, 26.75, 23.37; MS, m/z (relative intensity) 268 (M+,4.5), 239(0.03), 225(1.0), 211(0.6), 197(0.5), 183(0.4), 138(3.1), 124(5.5), 111(4.0), 110(7.4), 97(13.6), 96(26.8), 83(19.5), 82(86.0), 69(20.4), 68(20.1), 55(100.0), 54(9.4), 43(94.3), 41(93.4). Anal calcd for $C_{18}H_{36}O$:C,$^{80.52}$; H,13.52. Found: C,80.70; H,13.50.

We claim:

1. A method for the preparation of a carbocyclic ether having from 10 to 16 carbon atoms in the ring of the formula

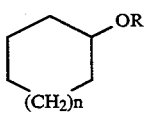

wherein R is a straight or branched ($C_3$–$C_6$) chain alkyl group or a benzyl group and n is from 5 to 11 carbon atoms, which method comprises:
   (1) reacting under an inert atmosphere a mixture consisting essentially of a carbocyclic alcohol of the formula

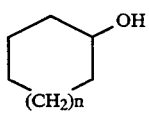

wherein n is from 5 to 11 carbon atoms, about 1.5–10 molar equivalents of said alcohol of a straight or branched ($C_3$–$C_6$) chain alkyl halide or a benzyl halide and a metal hydride;
   (2) destroying the excess metal hydride with an alcohol solvent
   (3) separating the ($C_{10}$–$C_{16}$) carbocyclic ether by extraction; and
   (4) distilling off the ($C_{10}$–$C_{16}$) carbocyclic ether in substantially pure form.

2. The method according to claim 1, wherein the alkyl halide is selected from the group consisting of alkyl iodide, alkyl bromide and alkyl chloride.

3. The method according to claim 1, where in step (2) the alcohol solvent is selected from the group consisting of ethanol or isopropanol.

4. The method according to claim 1, wherein the inert gas atmosphere consists essentially of argon.

5. The method according to claim 1, wherein the distilled ($C_{10}$–$C_{16}$) carbocyclic ($C_3$–$C_6$) alkyl ether or the distilled ($C_{10}$–$C_{16}$) carbocyclic benzyl ether is substantially free of unwanted byproducts.

6. The method according to claim 1, wherein the metal hydroxide ranges from about 1.5 to about 10 mol as equivalent of said carbocyolic alcohol.

7. The method for the preparation of n-propoxycyclodocecane according to claim 1 in which the alkyl halide is selected from the group consisting of 1-bromopropane and 1-iodopropane and the carbocyclic alcohol is cyclododecanol.

8. The method for the preparation of n-butoxycyclodocecane according to claim 1 in which the alkyl halide is selected from the group consisting of 1-bromobutane and 1-iodobutane and the carbocyclic alcohol is cyclododecanol.

9. The method for the preparation of 3-methylbutoxycyclododecane according to claim 1 in which the alkyl halide is selected from the group consisting of 1-bromo-3-methylbutane and 1-iodo-3-methylbutane and the carbocyclic alcohol is cyclododecanol.

10. A method for the preparation of n-hexyloxycyclododecane according to claim 1 in which the alkyl halide is 1-bromohexane and the carbocyclic alcohol is cyclododecanol.

11. A method for the preparation of n-propoxycyclotridecane according to claim 1 in which the alkyl halide is 1-iodopropane and the carbocyclic alcohol is cyclotridecanol.

12. A method for the preparation of n-propoxycyclotetradecane according to claim 1 in which the alkyl halide is 1-iodopropane and the carbocyclic alcohol is cyclotetradecanol.

13. A method for the preparation of ethoxycylopentadecane according to claim 1 in which the alkyl halide is iodoethane and the carbocyclic alcohol is cyclopentadecanol.

14. A method for the preparation of n-propoxycyclopentadecane according to claim 1 in which the alkyl halide is 1-iodproane and the carbocyclic alcohol is cyclopentadecanol.

* * * * *